USO05402886A

United States Patent [19]
McGlinch

[11] Patent Number: 5,402,886
[45] Date of Patent: Apr. 4, 1995

[54] STORAGE CONTAINER FOR INTRAVASCULAR CATHETERS

[75] Inventor: Timothy M. McGlinch, St. Paul, Minn.

[73] Assignee: Schneider (USA) Inc., Plymouth, Minn.

[21] Appl. No.: 93,070

[22] Filed: Jul. 16, 1993

[51] Int. Cl.⁶ .............................................. B65D 83/02
[52] U.S. Cl. ................... 206/364; 206/44.12; 229/242
[58] Field of Search ............... 206/364, 363, 44.12, 206/526; 229/240, 242, 243, 244

[56] References Cited

U.S. PATENT DOCUMENTS

| 1,989,806 | 2/1935 | Ischinger | 206/44.12 X |
| 2,343,222 | 2/1944 | Nelson | 229/244 |
| 2,442,699 | 6/1948 | Locke, Jr. | 229/242 X |
| 2,974,852 | 3/1961 | Huss et al. | 229/242 X |
| 3,315,875 | 4/1967 | Praetorius | 206/44.12 X |
| 3,606,135 | 9/1971 | Rosenburg, Jr. | 229/244 |
| 3,727,750 | 4/1973 | Petter | 206/63.2 R |
| 3,910,410 | 10/1975 | Shaw | 206/363 |
| 3,934,721 | 1/1976 | Juster et al. | 206/364 |
| 4,005,776 | 2/1977 | Seeley | 206/364 X |
| 4,106,621 | 8/1978 | Sorenson | 206/365 |
| 4,524,870 | 6/1985 | Roccaforte et al. | 229/242 |
| 4,550,834 | 11/1985 | Fletcher et al. | 229/242 X |

FOREIGN PATENT DOCUMENTS 1559843 1/1980 United Kingdom .
8907460 8/1989 WIPO .

OTHER PUBLICATIONS

Marcal ® Hankies Tissue Box.
Weight Watchers ® TV Dinner Box.

*Primary Examiner*—Steven N. Meyers
*Assistant Examiner*—Ted Kavanaugh
*Attorney, Agent, or Firm*—Peter C. Richardson; Lawrence C. Akers; Philip C. Strassburger

[57] ABSTRACT

A storage container for catheters having a separable portion of the front wall detachable from the container to ease removal of the catheter from the container is disclosed. The top portion is preferably separated from the side walls along external score lines at the intersection of the front and side walls. The separable portion of the front wall is preferably hinged on the bottom edge, which is perforated, easing complete separation of the separable portion from the front wall. Internal score lines on the inside surface of the separable portion of the front wall, parallel and proximate the external score lines are preferably provided to form flaps when the top portion of the front wall is detached from the container. The flaps prevent the top of the catheter package from falling out of the container. The separable portion of the front wall enables the catheter to be easily removed from the storage container without it being damaged.

3 Claims, 7 Drawing Sheets

STORAGE CONTAINER FOR INTRAVASCULAR CATHETERS

FIELD OF THE INVENTION

This invention relates to a storage container for intravascular catheters, and more particularly, a storage container for packaged intravascular catheters with an easy to remove flap, easing removal of the catheter without deformation.

BACKGROUND OF THE INVENTION

Intravascular catheters, such as diagnostic or guiding catheters, are typically supported on a long cardboard "card", placed in a sterile plastic wrap, and packaged in firm, paperboard boxes having hinged lids at the top through which the catheters are removed. Each box can contain one or up to five catheters in their individual plastic wraps. The hinged-lid of the box can include a cutout which allows the box to be hung on a wall of a catheter ("cath") lab once the lid is open. The boxes can also be stored in an upright shelf supported on the floor in the cath lab. When the particular catheter is needed, the plastic wrap containing the catheter is removed from the box and the catheter is removed from the wrap.

Because of the length of the catheter (typically between about 100-120 cm) and supporting card, removal from the tall box can be awkward. It is difficult to remove the catheter directly upward and out of the box, whether the box is hanging on a wall or resting on a shelf. The catheter package is thus usually removed in an arcuate fashion, bringing it into contact with the lip of the box. Although having some flexibility, if the catheter is bent too far against the lip of the hinged-lid opening, it will fold or "kink." This deformation can close the lumen or otherwise damage the catheter, rendering it useless for the intended procedure.

SUMMARY OF THE INVENTION

In accordance with the present invention, a storage container for catheters having front and rear walls with a separable top portion of the front wall, is provided. The front and rear walls are typically connected by side walls. The separable portion of the front wall is preferably defined by a first and second external score line positioned at the intersection of the front and side walls, and a hinge region preferably formed by a perforated line, which ease the separation of the separable portion. First and second internal score lines preferably extend along the internal surface of the separable portion of the front wall such that when the separable portion is separated from the front wall along the score lines, the score lines define a pair of flaps. Preferably, the first internal score line is essentially parallel to and proximate the first external score line and the second internal score line is essentially parallel to and proximate the second external score line. The flaps prevent the top of the catheter package from leaning out of the container after the separable portion is removed. The flaps are flexible so that when the catheter is removed, they give way, preventing kinking of the catheter. Detaching the separable portion from the container increases the opening through which the catheter can be removed. The catheter can then be removed from the container without interference which could damage the catheter.

DETAILED DESCRIPTION OF THE INVENTION

Figure 1:
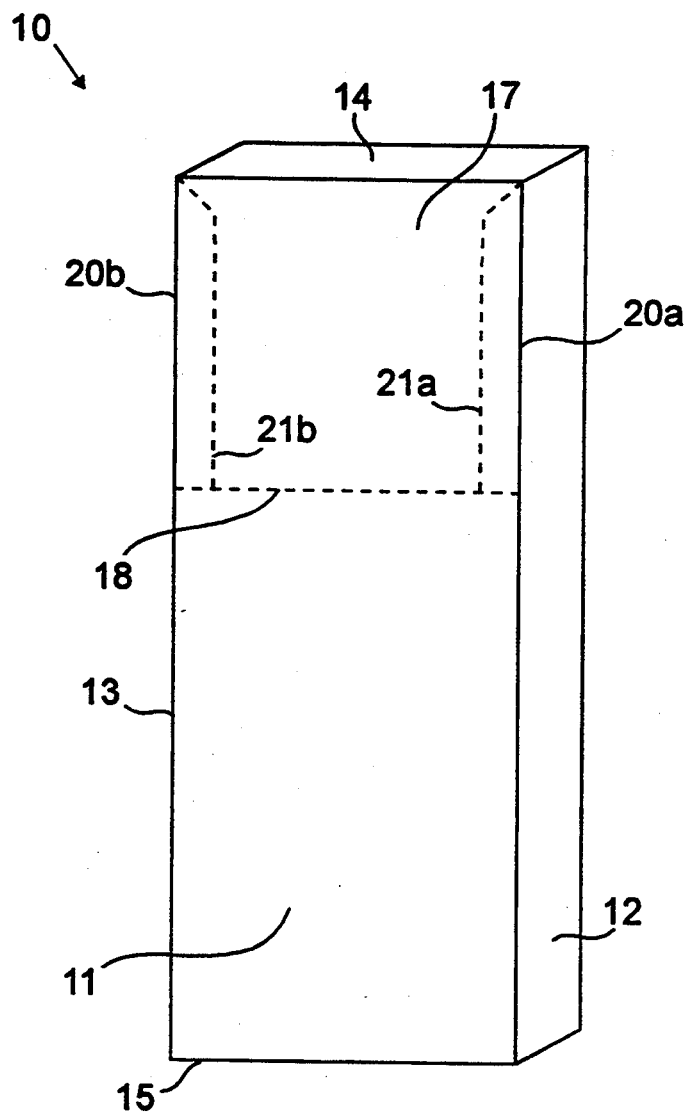
FIG. 1 is a front perspective view of the preferred embodiment of the storage container for intravascular catheters of the present invention, in the closed position.
Figure 2:
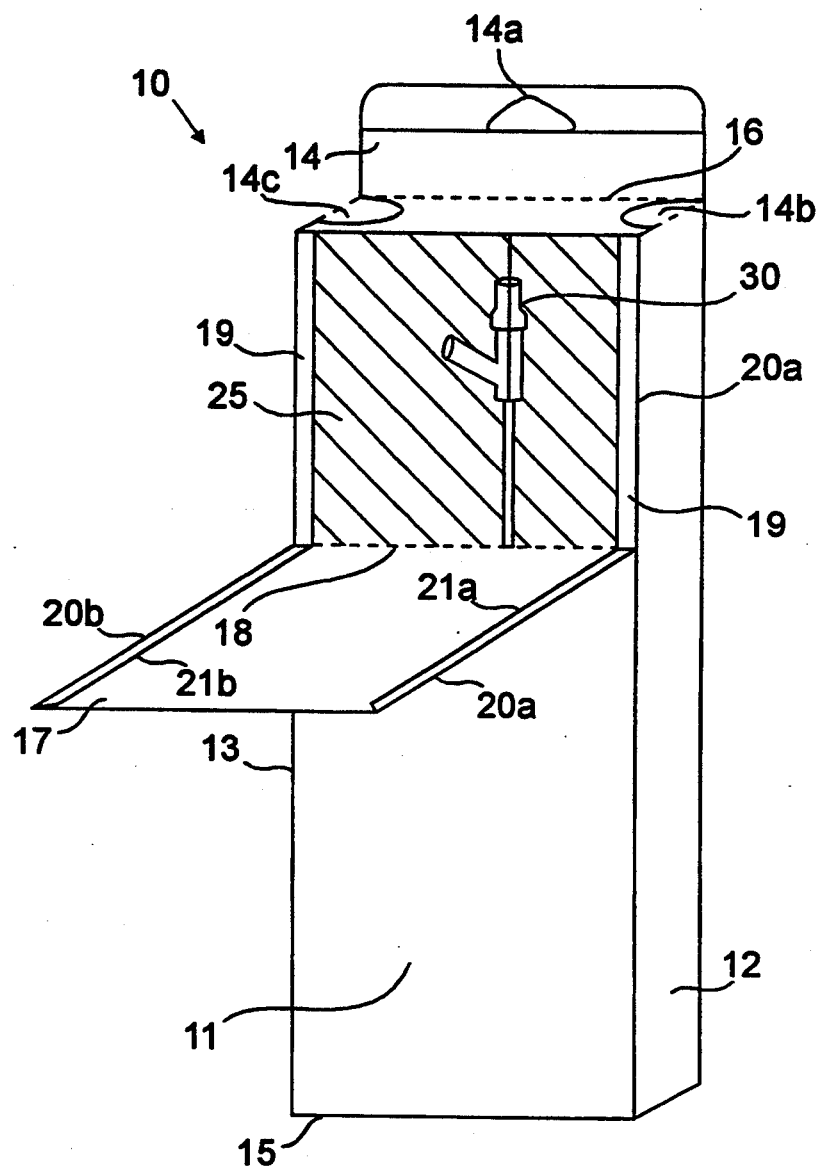
FIG. 2 is a front perspective view of the storage container of FIG. 1, with the separable portion of the front wall partially removed.
Figure 3:
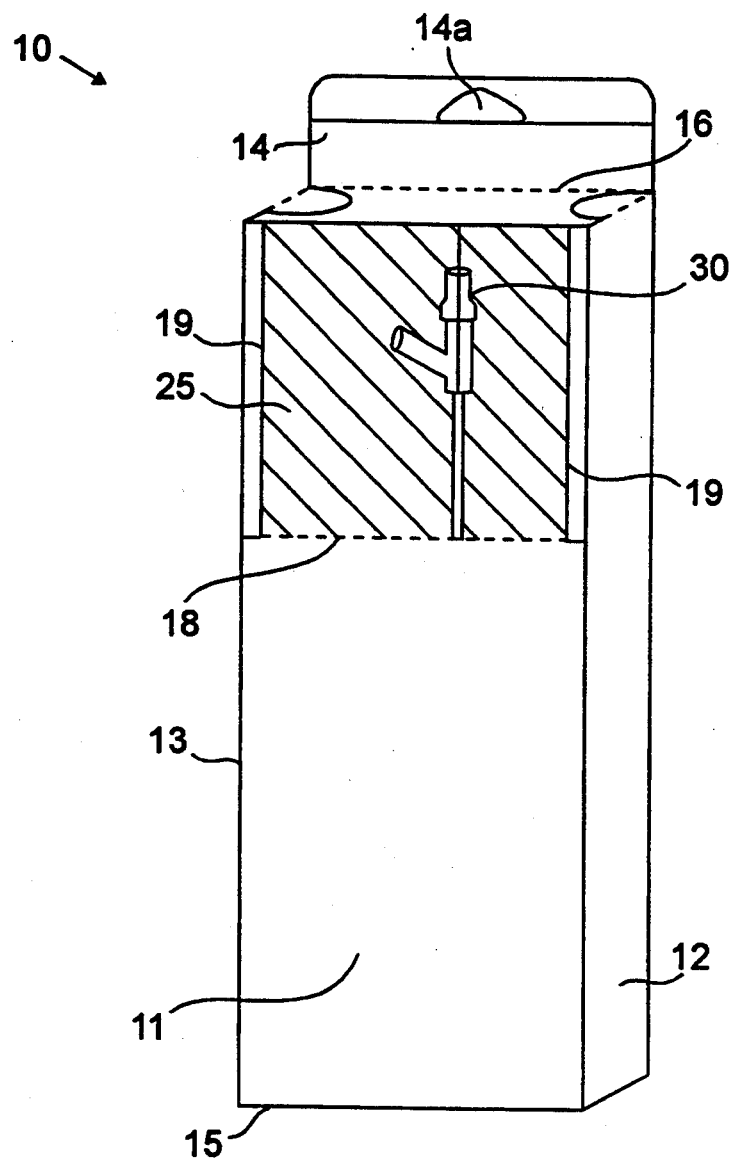
FIG. 3 is a front perspective view of the storage container of FIG. 1, with the top portion of the front wall totally removed.
Figure 4:
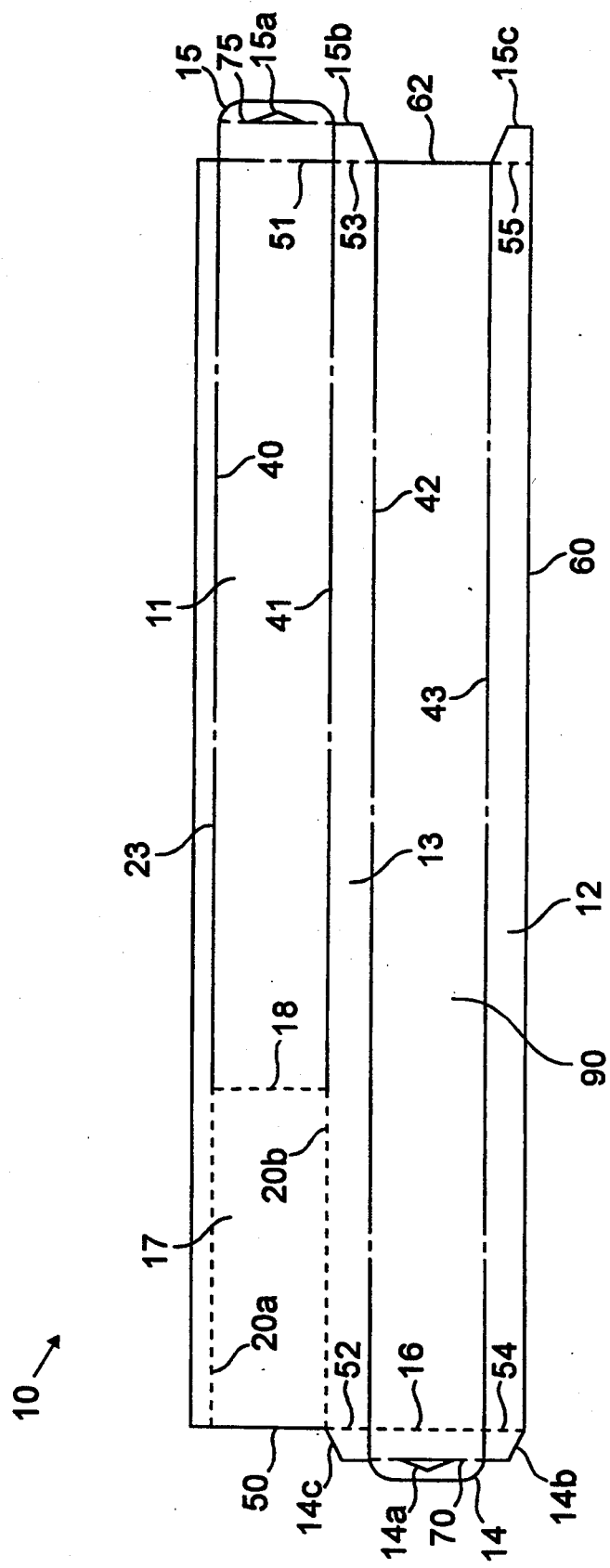
FIG. 4 is a plan view of the external side of a one-piece blank for forming the storage container of FIG. 1.
Figure 5:
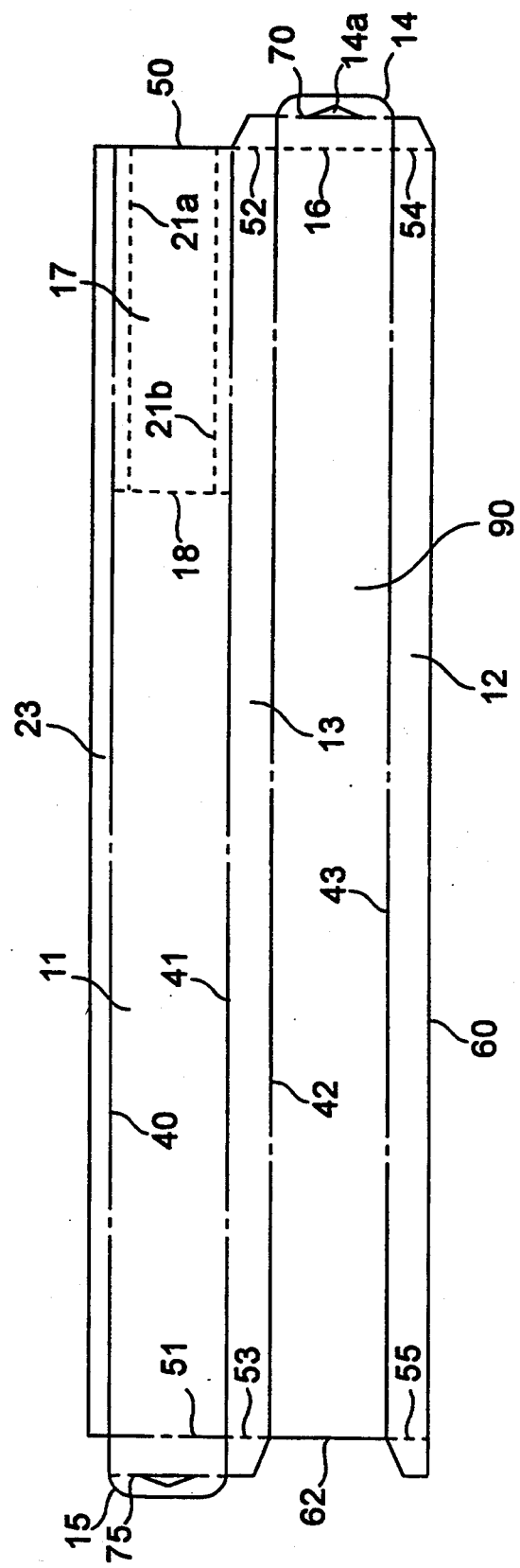
FIG. 5 is a plan view of the reverse side of the one-piece blank of FIG. 4, which forms the inside surface of the storage container of FIG. 1.

As shown in FIGS. 1-3, the preferred embodiment of the storage container 10 for intravascular catheters of the present invention preferably has a rectangular configuration, generally conforming to the shape of the card 25 (as shown in part in FIG. 2), which supports the catheter 30. The card 25 is packaged in a sterile plastic wrap (not shown). The storage container 10 includes a front wall 11, side walls 12 and 13 and two hinged-lids 14 and 15. Lid flaps 14b and 14c are preferably provided as well. (Lid flaps 15b and 15c are shown in FIGS. 4-5.) The hinged-lids 14 and 15 form the top and bottom walls of the storage container 10. At least one hinged-lid 14 preferably contains a cutout 14a to allow the storage container 10 to be hung from a wall in the cath lab, as shown in FIG. 2. The container 10 can also be stored in an upright shelf supported on the floor of the cath lab. The flexural hinge 16 of the top lid preferably consists of 1/16th inch perforations, for ease of detachment from the container 10, if desired, to ease removal of the card 25. The lid flaps 14b and 14c can be perforated as well. The container 10 is preferably about 49 inches high. The side walls 12 and 13 are preferably about 1.31 inches wide.

The upper portion of the front wall 11 includes a separable portion 17. The separable portion 17 is defined by a separation means preferably comprising a pair of external score lines 20a and 20b along the edge between the front wall 11 and the side walls 12 and 13, a pair of internal score lines 21a and 21b along the inside surface of the front wall 11, proximate and essentially parallel to the external score lines 20a, 20b, and a hinge region 18. The score lines 20a, 20b, 21a, 21b preferably penetrate about half the thickness of the walls. See FIGS. 1 and 2. The hinge region 18 is preferably formed by a perforated line perpendicular to the side walls 12 and 13, and extending from one side wall to the other. The perforations are preferably about 1/16th of an inch. The length of the separable portion is preferably about 13 inches from the top of the front wall. The walls of the container are preferably between about 0.024-0.022 inches thick.

The separable portion 17 can be disengaged by simply opening or removing the lid 14 and lid flaps 14b and 14c, and pulling the top of the separable portion 17 away from the front wall 11 along the pairs of score lines 20a, 21a and 20b, 21b. The separable portion 17 is thus "peeled" along the score lines down to the hinge region 18, as shown in FIG. 2. The separable portion 17 can be rotated downward about the hinge region 18 or can be preferably completely detached from the front wall 11 along the perforations forming the hinge line 18, as shown in FIG. 3. The opening provided by peeling back the separable portion 17 affords the necessary space for the catheter 30 to be removed in an arcuate fashion without becoming kinked or otherwise damaged.

When the separable portion 17 is pulled back along the pairs of score lines 20a, 21a and 20b, 21b, a pair of flaps 19 attached to the side walls 12 and 13 remain. The flaps 19 extend inwardly from the side walls 12 and 13. These flaps 19 are defined by the proximate pair of external and internal score lines 20a, 21a and 20b, 21b. The presence of these flaps 19 prevent the top of the card 25 from leaning out of the container 10 after the separable portion 17 is removed but prior to removal of the card 25 from the container 10. The flaps 19 are flexible so that when the catheter 30 is removed, they give way, easing removal of the card 25 from the container 10. If the container 10 is storing more than one catheter 30, the flaps 19 also maintain the remaining catheters in the container 10 after one is removed. The flaps 19 are preferably about 0.3125 inches wide and about 0.012 inches thick, where the walls of the box are about 0.024 inches.

FIGS. 4 and 5 show the external and internal surfaces, respectively, of a one-piece blank for forming the preferred embodiment of the storage container 10. The paperboard is preferably coated with solid bleach sulfate. The outline of the blank, the pair of score lines 20a, 20b and 21a, 21b and the perforated lines can all be cut in one-step by a die cutter machine, as is known in the art.

In FIG. 4, the front wall 11 is preferably defined by perforated line 51, edge 50, fold lines 40 and 41 and the external score lines 20a, 20b. The separable portion 17 of the front wall 11 is defined by the external score lines 20a, 20b and the hinge line 18, which is preferably perforated. One of the side walls 13 is defined by the external score line 20b, and fold lines 41, 42, 52 and 53. The other side wall 12 is defined by fold line 43, edge 60, and perforated lines 54 and 55. The rear wall 90 is defined by perforated line 16, fold lines 42 and 43 and edge 62. Also shown are perforated lines 70 and 75, which define a portion of the lids 14 and 15, and the lid flaps 14b, 14c, 15b and 15c. The bottom lid 15 also includes a cutout 15a. FIG. 5 shows the internal score lines 21a and 21b.

To form the storage container 10, the one-piece blank is folded along lines 40, 41, 42 and 43 and the inner wall 23 is glued to the side wall 12. The hinged-lids 14 and 15 are also folded about line 70 and flexural hinge 16 and lines 51 and 75, respectively, so as to form the top and bottom walls of the container 10. The lid flaps 14b, 14c, 15b, 15c, are folded as well.

Figure 6:
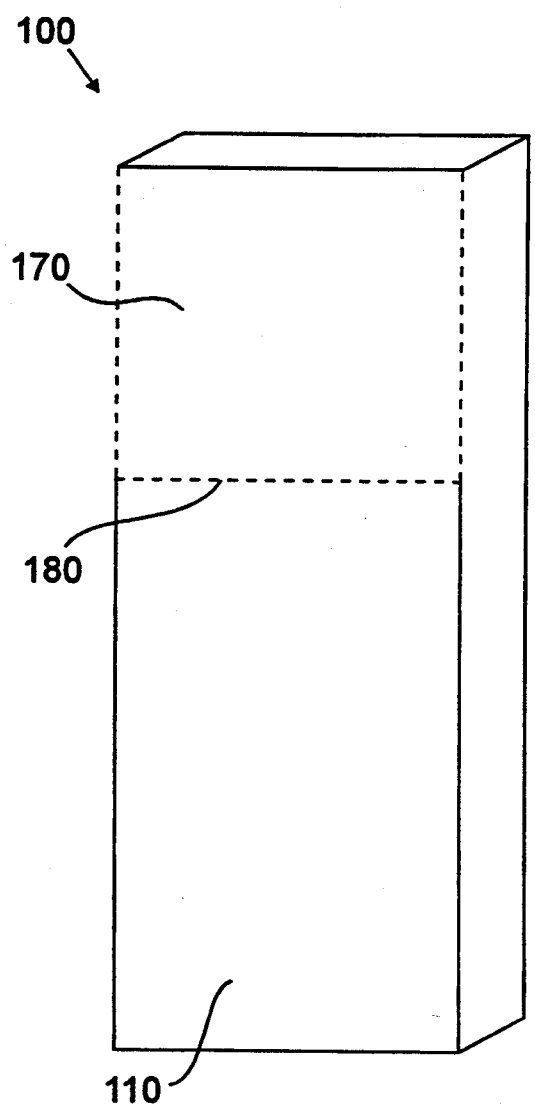
FIG. 6 is a front perspective view of a second embodiment of the storage container of the present invention in the closed position.
Figure 7:
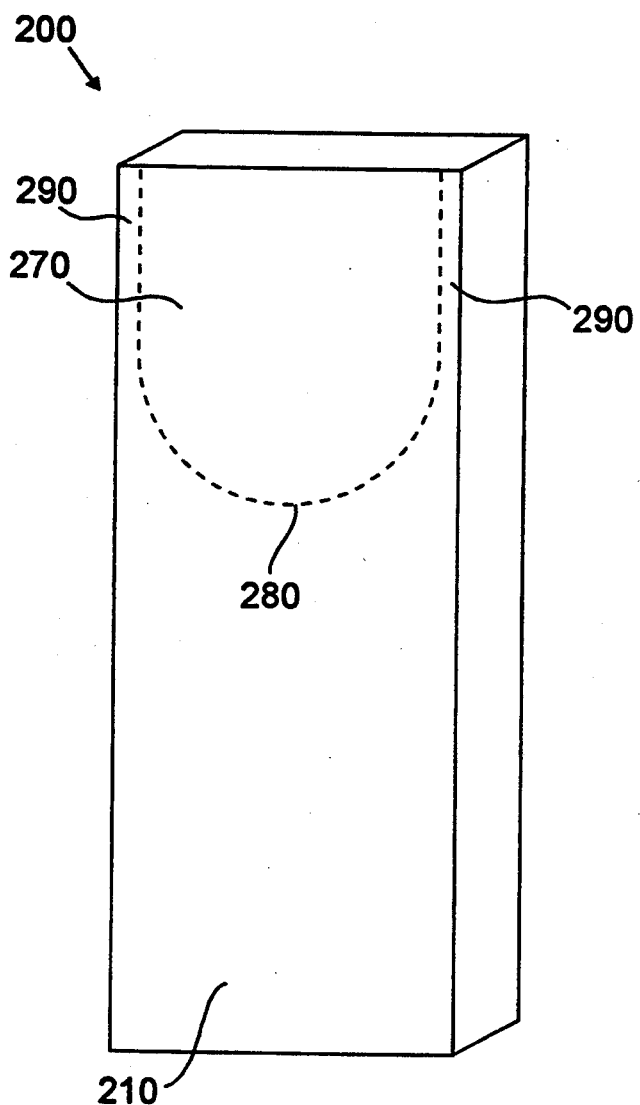
FIG. 7 is a front perspective view of a third embodiment of the storage container of the present invention in the closed position.

While the use of the pairs of score lines described above is preferred, other means for separating the separable portion 17 may be provided. For example, only the single pair of score lines 20a, 20b, at the intersection between the front wall 11 and side walls 12 and 13, could be provided. Instead of score lines, perforations or a zipper-cut could be provided along the edge of the front wall, as well. FIG. 6 shows another embodiment of the present invention where the separable portion 170 of the storage container 100 is completely defined by a perforated line 180. The perforated line 180 can run along a portion of each edge between the front wall 11 and side walls 12 and 13, and between them, as shown in FIG. 6. No flaps, such as the flaps 19 shown in FIGS. 2 and 3, would be formed. FIG. 7 shows another embodiment where a portion of the perforated line 280 could also run proximate the edges of the front wall 210. The sections 290 of the front wall 210 remaining after the separable portion 270 is detached would keep the catheter 30 within the container 10 prior to its removal. The perforations in all cases would preferably be 1/16th inch cut. The excessive use of perforations may not be desirable, however, because tearing of the paperboard, even along perforated lines, could cause small portions of the paperboard to detach, causing contamination problems in the cath lab. A storage container 10 with excessive tear lines may not be aesthetically pleasing, either.

It will be apparent to those skilled in the art that the invention described herein can be practiced by other than the embodiments described above, which are presented for the purposes of illustration and not of limitation, and the present invention is limited only by the claims which follow.

What is claimed is:

1. A storage container for catheters comprising:
a single layered front wall having a thickness, and a rear wall;
first and second side walls connecting the front and rear walls;
a hinged lid for closing a top end of the container, the hinged lid being part of the rear wall;
a separable portion of the front wall in a top portion of the front wall proximate and separate from the hinged lid, providing an opening for removing a catheter stored within the container, the separable portion being defined by a first external score line extending along a first external edge between the front wall and the first side wall, a second external score line extending along a second external edge between the front wall and the second side wall, a first internal score line extending along an internal surface of the front wall, proximate and essentially parallel to the first external score line, a second internal score line extending along the internal surface of the front wall, proximate and essentially parallel to the second external score line, each of the score lines penetrating partially through the thickness of the front wall, and a perforated line extending from the first edge to the second edge, the perforated line being essentially perpendicular to the first and second edge and intersecting the score lines, such that when the separable portion is removed from the front wall a first flexible flap defined by the first internal and external score lines and a second flexible flap defined by the second internal and external score lines are formed, the flaps extending from the first and second edges into the opening, the flaps having a thickness less than the thickness of the front wall.

2. A storage container for catheters comprising:
a single layered front wall having an upper portion proximate a top end of the container and a thickness;

a rear wall;

first and second side walls connecting the front and rear walls;

the upper portion of the front wall comprising a separable portion providing an opening for removing a catheter stored within the container;

the separable portion being defined at least in part by a first external score line proximate a first external edge between the front wall and the first side wall;

a second external score line proximate a second external edge between the front wall and the second side wall;

a first internal score line extending along an internal surface of the front wall, proximate the first external score line, a second internal score line extending along the internal surface of the front wall, proximate the second external score line;

each of the score lines penetrating partially through the thickness of the wall such that when the separable portion is removed from the top portion, a first flexible flap defined by the first internal and external score lines and a second flexible flap defined by the second internal and external score lines extend into the opening, the flaps having a thickness less than the thickness of the front wall;

wherein the separable portion is further defined by a hinge region in the front wall comprising a perforated line extending between the score lines about which the separable portion can rotate.

3. A storage container for catheters comprising:

a single layered front wall having an upper portion proximate a top end of the container and a thickness;

a rear wall;

first and second side walls connecting the front and rear walls;

the upper portion of the front wall comprising a separable portion providing an opening for removing a catheter stored within the container;

the separable portion being defined at least in part by a first external score line proximate a first external edge between the front wall and the first side wall;

a second external score line proximate a second external edge between the front wall and the second side wall;

a first internal score line extending along an internal surface of the front wall, proximate the first external score line, a second internal score line extending along the internal surface of the front wall, proximate the second external score line;

each of the score lines penetrating partially through the thickness of the wall such that when the separable portion is removed from the top portion, a first flexible flap defined by the first internal and external score lines and a second flexible flap defined by the second internal and external score lines extend into the opening, the flaps having a thickness less than the thickness of the front wall;

further comprising a hinged lid on the top end of the container, the hinged lid being part of the rear wall and separate from the separable portion of the front wall, the hinged lid comprising a section defining a cutout to allow the container to be hung.

* * * * *